United States Patent [19]
Butler et al.

[11] Patent Number: 5,902,766
[45] Date of Patent: May 11, 1999

[54] ALUMOXANES, CATALYSTS UTILIZING ALUMOXANES AND POLYMERS THEREFROM

[75] Inventors: Jeffrey Harold Butler, Baytown; Terry John Burkhardt, Kingwood, both of Tex.

[73] Assignee: Exxon Chemical Patents Inc., Houston, Tex.

[21] Appl. No.: 08/532,039

[22] Filed: Sep. 21, 1995

Related U.S. Application Data

[63] Continuation of application No. 08/180,171, Jan. 11, 1994, abandoned.

[51] Int. Cl.⁶ ........................................... C08F 4/42
[52] U.S. Cl. ..................... 502/152; 502/120; 526/160; 526/943; 556/179
[58] Field of Search ...................... 502/120, 152; 526/160; 556/179

[56] References Cited

U.S. PATENT DOCUMENTS

| | | | |
|---|---|---|---|
| 4,730,071 | 3/1988 | Schoenthal et al. | 556/179 |
| 4,730,072 | 3/1988 | Schoenthal et al. | 556/179 |
| 4,897,455 | 1/1990 | Welborn, Jr. | 526/129 |
| 4,952,540 | 8/1990 | Kioka et al. | 502/9 |
| 4,990,640 | 2/1991 | Tsutsui et al. | 556/181 |
| 5,015,749 | 5/1991 | Schmidt et al. | 556/179 |
| 5,017,714 | 5/1991 | Welborn, Jr. | 556/12 |
| 5,026,798 | 6/1991 | Canich | 526/127 |
| 5,041,583 | 8/1991 | Sangokoya | 556/179 |
| 5,057,475 | 10/1991 | Canich et al. | 502/104 |
| 5,064,797 | 11/1991 | Stricklen | 502/111 |
| 5,066,631 | 11/1991 | Sangokoya et al. | 502/152 |
| 5,070,160 | 12/1991 | Tomotsu et al. | 526/165 |
| 5,091,352 | 2/1992 | Kioka et al. | 502/103 |
| 5,099,050 | 3/1992 | Sangokoya | 556/179 |
| 5,145,819 | 9/1992 | Winter et al. | 502/117 |
| 5,157,137 | 10/1992 | Sangokoya | 556/179 |
| 5,235,081 | 8/1993 | Sangokoya | 556/179 |
| 5,240,894 | 8/1993 | Burkhardt et al. | 502/108 |
| 5,308,815 | 5/1994 | Sangokoya | 502/104 |
| 5,332,706 | 7/1994 | Nowlin et al. | 502/107 |

FOREIGN PATENT DOCUMENTS

| | | |
|---|---|---|
| 2033805A1 | 8/1991 | Canada . |
| 0367503A1 | 5/1990 | European Pat. Off. . |
| 0561476A1 | 9/1993 | European Pat. Off. . |
| 3-271295 | 12/1991 | Japan . |
| 4-49293 | 2/1992 | Japan . |

*Primary Examiner*—David W. Wu
*Attorney, Agent, or Firm*—Catherine L. Bell; Paige Schmidt

[57] ABSTRACT

A catalyst which exhibits superior control of product particle size in the insertion polymerization of alpha-olefins is described as transition metal compounds which associate with non-coordinating alumoxane anions which are dispersed throughout the interior of a silica support in the form of particles which are less than or equal to about 50 Å (5 nanometers) in diameter. This catalyst is capable of gas phase (e.g. heterogeneous) polymerization of propylene into product granules with a high degree of control over granule particle size distribution and bulk density.

15 Claims, No Drawings

ALUMOXANES, CATALYSTS UTILIZING ALUMOXANES AND POLYMERS THEREFROM

This is a continuation of application Ser. No. 08/180,171, filed Jan. 11, 1994, now abandoned.

FIELD OF THE INVENTION

This invention relates to supported and unsupported alumoxanes, particularly alkyl-alumoxanes, which can be used in combination with a mono-, bis- or tris-cyclopentadienyl transition metal compounds as polymerization catalysts for olefins. These catalyst systems are capable of polymerizing olefinic monomers into granules having a narrow molecular weight distribution, low ash content and superior bulk density. Likewise these catalyst systems also provide improved sustained operability under reactor conditions.

BACKGROUND OF THE INVENTION

Over the past 10 years a new generation of catalysts which utilize alumoxane as an activator for mono, bis or tris cyclopentadienyl transition metal compounds ("metallocenes") has been developed in striking contrast to the previous Ziegler-Natta catalysts which utilize aluminum alkyls as the activators. This new generation of catalysts demands more efficient methods for producing and utilizing alumoxanes. It is known that alumoxanes can be produced generally by contacting a trialkylaluminum with water under controlled reaction conditions to produce an alumoxane. However, in recent years this simple method has been expanded. WO92/21685, U.S. Pat. No. 4,908,463, U.S. Pat. No. 4,937,363, U.S. Pat. Nos. 4,968,827, 4,924,018, 5,003,095, 5,041,583, 5,066,631, 5,099,050, 5,157,137, 4,544,762, 5,084,585 and 5,064,797 all disclose various methods of producing alkylalumoxanes particularly methylalumoxane, to be used as a catalyst itself or as an activator for various catalysts such as mono, bis or tris cyclopentadienyl transition metal compounds. U.S. Pat. No. 4,952,540 discloses finely divided alumoxanes having an average particle size of 5 to 200 micrometers and a surface area of 20 to 1000 meters square per gram used in conjunction with a cyclopentadienyl transition metal compound to produce a polymer having high bulk specific gravity (also called bulk density). U.S. Pat. No. 5,015,749 discloses alumoxanes placed on a porous organic or inorganic aqueous imbiber material containing water. The support has an average surface area of 1 $m^2/g$ to 1200 $m^2/g$ and an average pore diameter of about 15 to about 10,000 angstroms.

While there are a multitude of references teaching various methods to produce alumoxanes it has not yet been discovered how to manipulate alumoxanes, specifically for maximizing supported catalytic activity and polymer product characteristics. Thus, a method is desired for manipulating alumoxane which produces catalysts with controlled bulk density, ash content, polymer particle sizes, and polymer particle size distribution.

During the polymerization process polyolefin catalyst systems comprised of co-catalyst/catalyst in a support become shattered into tiny fragments which end up being uniformly scattered throughout the final polymer product. The amounts of the individual residual elements relative to the total amount of polymer product are collectively referred to as the ash content. This is an important parameter from two points of view. First in some end product applications such as food packaging there are limits on the acceptable amount of ash, but even more important is the economic factor through the standpoint of catalyst efficiency. Lower ash contents are a direct effect of being able to make more polymer using less catalyst. Commercial polyolefin production reactors can be adversely influenced by inconsistencies in the individual behavior of any particular catalyst. A typical problem situation is one in which the catalytically active species become inhomogeneously distributed within the reactor to result in the build up of local "hot" spots. Here the temperatures get so high, that the product polymer melts and fuses together eventually forming internal chunks and causing reactor fouling. To ensure reactor operability it is preferred to run a catalyst system which maintains homogeneity of the active species throughout the reactor.

The ideal production scheme optimizes the final product properties as well as the physical form of the final product. Although the former of these can be optimized by means of chemistry and reactor conditions, the latter is controlled more by the fragmentation properties of the catalyst carrier which, in turn, are controlled by the dispersion of the catalyst on and throughout the carrier. Thus an important consideration in olefin polymerization has been developing methods for loading the carrier with catalyst. The location and chemical nature of the catalytically active species in the carrier microstructure is an important consideration. The exact arrangement of active catalyst sites within the carrier provides ultimate control over the carrier fragmentation behavior and, subsequently, over the physical form of the final product. Consequently, unambiguous knowledge of the supported catalyst microstructure can lead to control of final polymer product morphology, independent of the nature of the polymer being produced. This, in turn, provides control over the product bulk density as well as reactor operability and, as such, represents an improvement over the existing art.

In such reactor systems the amount of cocatalyst required to activate the catalyst is measured as the aluminum moles to metal moles ratio [Al/M]. Depending on the particular process and catalyst there is a wide dispersion in values for this ratio, but often it is over 1000:1 and is typically over 500:1. Also large variations in bulk density values as well as intermittent reactor fouling are two problems often associated with alumoxane activated catalysts when they are supported on a silica carrier and used in a slurry or gas phase process.

SUMMARY OF THE INVENTION

This invention relates to alumoxanes, and methods to produce catalyst compositions comprising alumoxane ("AlO"). This invention further relates to methods for producing narrow molecular weight distribution polymer with good bulk density, controlled ash content and controlled particle size and particle size distribution. Likewise, this invention relates to alumoxane compositions comprising greater than(50% by weight 100 Angstrom (10 nanometers) or smaller alumoxane particles, also called primary particles.

The present invention further provides a class of catalysts which fragment the catalyst carrier in a way that improves the morphological form of final product granules.

In one embodiment, the present invention relates to a polymerization catalyst that can be used to produce preselected polymer molecular weight distributions (MWD's) comprising a support containing a transition metal compound and an alumoxane. This catalyst system can produce a narrow MWD of Mw/Mn=1–3, and a consistently uniform granular product distribution with a bulk density greater than 25 $lb/ft^3$ (0.4 g/cc).

DETAILED DESCRIPTION OF THE PREFERRED EMBODIMENTS

In a more specific embodiment, the present invention relates to a polymerization catalyst comprising a silica open-cell foam with a fine mesopore size (<20 nm) and high surface area (200–500 $m^2$ $g^{-1}$) having transition metal catalyst cations associated with alumoxane anion particles, said particles which have a bimodal particle size distribution (the first mode typically centers at 5 nanometers and the second mode typically centers at 20 nanometers). The first fraction, comprising alumoxane particles of about 19 nanometers or less, preferably having an average diameter of 5 nanometers or less, is impregnated within the mesopores of the carrier, preferably a silica carrier granule, while the second fraction, which comprises alumoxane particles of about 20 nanometers or greater, is absent or if a small portion is present they are distributed over the exterior of the carrier, preferably a silica granule.

In a preferred embodiment a freshly prepared catalyst, (e.g. a catalyst which has neither been exposed to reactive contaminants nor contacted with a olefinic monomer feed) comprises a transition metal compound associated with at least 90%, preferably more than 98%, of the primary ($\leq 19$ nm) alumoxane cocatalyst particles, which occupy and are uniformly dispersed throughout the silica mesopores. Less than 10% of the transition metal compound associates with larger (greater than or equal to 20 nm) alumoxane anion particles. X-ray Photoelectron Spectroscopy (XPS), Static Secondary Ion Mass Spectrometry (SSIMS), electron micrographs and microanalytical x-ray spectra of such a catalyst supported on a mesoporous silica show that more than 90% of transition metal catalyst cations are dispersed throughout the interstices of the silica carrier while being associated with the small ($\leq 19$ nm) alumoxane anion particles, and less than 10% are dispersed across the internal macropores of the silica carrier, as well as resting on the silica carrier granule exterior while being associated with larger ($\geq 20$ nm) alumoxane particles. This preferred embodiment minimizes porous, low bulk density, final polymer product granules, as well as macroscopic (>2 mm) chunks of product, and maximizes the relative amount of individual, high bulk density product granules. The physical size, and consequently, the relative dispersion of catalyst activated alumoxane particles throughout the silica carrier interior accounts for the relatively low Al/M ratios, as well as control over final product granule morphology and, consequently, over bulk density.

This invention relates in part to the discovery that the size, dispersion and degree of aggregation into fractal networks of alumoxane particles influence the usefulness of any alumoxane used in combination with transition metal compounds to produce an active olefin catalyst system. Preferred compositions of alumoxane include those with more "small" particles than large particles to produce polymer granules which are small and uniform in size. After careful study of many methyl alumoxanes, we have determined that, in general, there exists an essentially bimodal size distribution of colloidal alumoxane particles in suspension. The first group comprises particles having an average diameter of less than about 50 angstroms (5 nanometers), and the other group is that fraction of particles having an average diameter greater than about 200 angstroms (20 nanometers). For purposes of this invention the first fraction which has an average particle diameter size of about 5 nanometers is herein defined to include particles up to about 19 nanometers in size. Likewise the second fraction which has an average particle size of about 20 nanometers or greater is defined to include particle of 20 nanometer diameter or more. We have further discovered that by controlling the ratio or amount of large and small particles present in an alumoxane suspension, that the supported catalyst activity and final polymer product characteristics can be dramatically enhanced. In particular, when utilizing alumoxane suspensions where the larger particles have been allowed to settle out, or have otherwise been removed, i.e. the suspension was enhanced with small particles, the catalysts had greater activity and the polymer produced had little or no reactor fouling and dramatically improved particle size and particle size distributions. When the alumoxane was drawn from suspensions that had a random distribution of large and small particles, lower catalyst activity, higher reactor fouling, and much different particle sizes and distributions were observed.

Thus, preferred embodiments of this invention utilize alumoxane where particles larger than the mesopore size of the support have been removed or preferably not allowed to form in the first place. Methods for removing the larger particles include filtering out large particles, centrifuging to separate the large from the small particles, gel chromatography to separate the particles, allowing the suspension to settle and drawing from the top portion or from the clear portion of the suspension, allowing the large particles to settle and drawing from the non-settled are and the like.

In another preferred embodiment this invention also provides new compositions of matter comprising alumoxane particles and or alumoxane-transition metal complexes having greater than 50% by weight particles having an average diameter of about 50 angstroms (5 nanometers) or less, most preferably greater than about 90%, preferably about 100%. Percent by weight ("% by weight" or "wt. %.") is herein defined to include only the weight of the alumoxane and not the weight of the solvent or carrier. % by weight is calculated by dividing the weight of the first fraction by the weight of the total alumoxane present. The weight of the two fractions can be determined by:

(1) removing the secondary particles (for example filtering out particles larger than 190 angstroms);
(2) removing any carrier from the secondary particles (for example evaporating off any solvent in the filter paper;
(3) weighing the secondary particles (for example weighing the filter paper containing secondary particles then subtracting the weight of the filter paper);
(4) removing any carrier from the primary particles (for example centrifuging the filtered solution, pulling off the solvent portion then evaporating off any remaining solvent); and
(5) weighing the primary particles (for example weighing the remaining solid produced in step 4). The weight percent is then determined by dividing the weight of the primary particles by the sum of the weight of the primary and secondary particles.

In addition, this invention further provides in a preferred embodiment for alumoxane compositions and alumoxane-transition metal compound complexes wherein the average particle size is less than or equal to about 50 angstroms.

These alumoxanes can further be placed on various supports such as silica, alumina, ceramics, organics, polymeric and other supports known to those of ordinary skill in the art that have been appropriately dried, dehydrated or otherwise treated. In a preferred embodiment the alumoxanes of the invention can be utilized in the support technique disclosed in U.S. Pat. No. 5,240,894 which is incorporated by reference herein.

Typically the support can be any organic or inorganic, inert solid, particularly, porous supports such as, silicates, e.g. talc, etc. inorganic oxides, and resinous support materials such as polyolefins. Suitable inorganic oxide materials which are desirably employed include Groups 2, 3, 4 or 5 metal oxides such as silica, alumina, silica-alumina, and mixtures thereof. Other inorganic oxides that may be employed either alone or in combination with the silica, alumina or silica-alumina are magnesia, titania, zirconia, and the like. Other suitable support materials can be employed such as, finely divided polyolefins, such as polyethylene.

One parameter for classifying the pore structure of catalyst support materials is the average pore diameter, $d_p$, and its relation to the size of the adsorptive species determines how well that species can be distributed throughout the pore structure. Porous adsorbents are classified according to their average pore diameter based on general differences in the shape of gas adsorption isotherms (M. M. Dubinin, Advan. Colloid Interface Sci. 2,217(1968)):

| Classification | Average Pore Diameter, $d_p$ | Specific Surface Area, s |
| --- | --- | --- |
| microporous | <30 Å | >500 m$^2$/g |
| mesoporous | 30 < $d_{p_e}$ < 2000 Å | 10 < s < 500 m$^2$/g |
| macroporous | >2000 Å | s < 10 m$^2$/g |
| Davison 948 | 120 < $d_p$ < 210 Å | s ≈ 360 m$^2$/g |

According to this classification scheme then, most polymerization grade silica gels are described as having an intermediate porosity. Preferred open-cell foams used in this invention are a general class of highly porous materials with a fine mesopore size (preferably less than 50 nm, more preferably from 6 to about 40 nm, and even more preferably from 10 to 30 nm with about 20 nm being especially preferred) a wide range of macropore sizes (0.05 $\mu$m–1.5 $\mu$m), and high surface area 200–500 m$^2$ g$^{-1}$).

Pore structure parameters such as s, $d_p$, and pore size distributions can be determined by gas adsorption and desorption for microporous and intermediate porosity materials (K. Unger, Angew. Chem. Internat. Edit. 11(4), 267 (1972)), while macroporosity is best determined by mercury porosimetry (W. C. Conner, E. L. Weist, A. H. Ali, M. Chiovetta and R. L. Laurence, "Morphological Influences in the Gas-Phase Polymerization of Ethylene Using Supported Chromium Catalysts", in *Transition Metal Catalyzed Polymerizations. Ziegler-Natta and Metathesis Polymerization*, R. P. Quirk,Ed., Cambridge University Press, New York (1988), pp. 417–427) all of which are incorporated by reference herein.

Preferred supported polymerization catalysts of this invention have unique compositions characterized by several properties which lead to improved activity maintenance and, consequently, control over polymer product granule particle size (and hence the bulk density), enhanced reactor operability (by reducing fouling) and efficient use of cocatalyst (resulting in significantly reduced ash levels and Al/M ratios). The greater the degree of dispersion of the catalytically activated small particle MAO fraction (average of 5 nm or less in diameter) within the mesopore structure, i.e., onto the internal surface area of the support, and the lesser the degree of dispersion of the large particle MAO fraction on the external surface area of the support, the better will be the catalytic performance.

The activity of a catalyst is a measure of its ability to convert monomer feed into products. While a catalyst may have a high activity, the products formed may not be necessarily the desired products. Activity maintenance concerns the ability of the catalyst to maintain a portion of its activity over time at conversion conditions, other variables remaining constant. Upon exposure to feed, catalyst impregnated carrier particles grow into polymer granules whose sizes, shapes and voids content determine the final product bulk density. In the case of supported polyolefin catalysts, the activity maintenance and, in turn, product granule morphology is determined in large part by the fragmentation of the support, a process during which fresh catalyst surface is continuously exposed. Carrier fragmentation is controlled by the silica particle microstructure (macropore and mesopore distributions), and the arrangement of active species within the pore structure. The improvement in activity maintenance is manifested in preferred catalysts systems of this invention in that they provide a bulk density in excess of 25 lb/ft$^3$ (0.4 g/cm$^3$)upon exposure to typical reactor operating conditions.

In a preferred embodiment, the following combination of steps is performed, i.e., (1) combining one or more cyclopentadienyl transition metal compounds with an alumoxane suspension having at least 50% by weight or more of particles of alumoxane having an average diameter of 50 Å or less (5 nanometers or less), (2) adding dehydrated carrier having a meseporous classification as defined above (3) evaporating or heating the resulting slurry to remove liquid solvent (4) further heat to desolvate the solid supported catalyst and thus remove any residual solvent trapped in the pores prior to use. A fifth (5) optional step involves prepolymerizing the catalyst with olefinic monomer. In a preferred embodiment one may obtain a polymer product in the absence of reactor fouling, by utilizing the supported catalyst (as is or prepolymerized), the cocatalyst and scavenger aluminum alkyl or organoaluminum during polymerization.

The supported reaction product is isolated, and dried to remove residual solvent. The supported catalyst product formed can be employed as a sole catalyst component for the polymerization of olefins containing from about 2 to about 30 carbon atoms, or, in the preferred alternative, it can be employed with an organometallic cocatalyst such as triethylaluminum or full MAO.

In a preferred embodiment the carrier is thoroughly dehydrated prior to loading, preferably to contain about or less than 1% loss on ignition (LOI). Thermal dehydration treatment may be carried out in vacuum or while purging with a dry inert gas such as nitrogen at a temperature of about 100° C. to about 10000° C., and preferably, from about 300° C. to about 800° C. Pressure considerations are not critical. The duration of thermal treatment can be from about 1 to about 24 hours. However, shorter or longer times can be employed provided equilibrium is established with the surface hydroxyl groups.

Dehydration can also be accomplished by subjecting the carrier to a chemical treatment in order to remove water and reduce the concentration of surface hydroxyl groups. Chemical treatment converts all water and hydroxyl groups in the oxide surface to inert species. Useful chemical agents are for example, chlorosilanes such as $SiCl_4$, trimethylchlorosilane, dimethylaminotrimethylsilane and the like. The chemical dehydration is accomplished by slurrying the inorganic particulate material such as, for example silica, in an inert low boiling hydrocarbon, such as for example, hexane. During the chemical dehydration treatment, the silica should be maintained in a moisture and oxygen free atmosphere. To the silica slurry is then added a low boiling inert hydrocarbon solution of the chemical dehydrating agent, such as, for example dichlorodimethylsilane. The solution is added slowly to the slurry. The temperature ranges during chemical dehydration reaction can be from about 25° C. to about 120° C., however, higher and lower temperatures can be employed. Preferably, the temperature will be about 50° C. to about 70° C. The chemical dehydration procedure should be allowed to proceed until all the moisture is removed from the particulate support material as indicated by cessation of gas evolution. Normally, the chemical dehydration reaction will be allowed to proceed from about 30 minutes to about 16 hours, preferably, 1 to 5 hours. Upon completion of the chemical dehydration, the solid particulate material is filtered under a nitrogen atmosphere and washed one or more times with a dry, oxygen free inert solvent. The wash solvents as well as the diluents employed to form the slurry and the solution of chemical dehydrating agent, can be any suitable inert hydrocarbon. Illustrative of such hydrocarbons are heptane, hexane, toluene, isopentane and the like.

Illustrative examples of useful solvents include the alkanes such as pentane, isopentane, hexane, heptane, octane, and nonane; cycloalkanes such as cyclopentane and cyclohexane; and aromatics such as benzene, toluene, ethylbenzene and diethylbenzene.

The amount of alumoxane and metallocene usefully employed in preparation of the supported catalyst system can vary over a wide range. However, an aluminum to transition metal molar ratio of about 12:1 to about 1000:1 is preferred; more preferably, a ratio of about 100:1 to about 500:1 is employed, even more preferably a ratio of 12:1 to about 50:1. The weight ratio of metallocene to support is typically 0.01 to 0.20, most preferably 0.05 to 0.10.

At all times, the individual ingredients as well as the recovered catalyst component are protected from oxygen and moisture. Therefore, the reactions must be performed in an oxygen and moisture free atmosphere and recovered in an atmosphere which is moisture and oxygen free. Preferably, therefore the reactions are performed in the presence of an inert dry gas such as, for example nitrogen. The recovered catalyst is maintained in a nitrogen atmosphere.

Prepolymerization of the supported catalyst can be employed to strengthen catalyst particles and enhance particle size control of the final polymer formed. The supported catalyst is reslurried in isopentane or a MAO non-solvent and prepolymerized with an olefin monomer, such as ethylene gas. The prepolymerized catalyst is then decanted, washed with isopentane, and dried in a vacuum at room temperature in order to isolate the supported, prepolymerized catalyst. The prepolymerization typically occurs at a temperature of −15° C. to +30° C., preferably less than 25° C. for about 75 minutes. The amount of prepolymer can be varied from 10% to 300% of the supported catalyst weight, most preferably 50–150%. As will be apparent to those of any skill in the art any other support method may also be used.

In situations where the alumoxane is supported by any technique, it is preferred that the alumoxane be present in the same or a substantially higher concentration "inside" the support than "outside" the support. By inside the support we mean the internal surface area of the support granule. By outside the support we mean on the external surface of the support granule and the surface of any macropores. By total surface area we mean both the internal and external surface area of the support. Where the transition metal compound is also supported, it is still preferred that the alumoxane be present at substantially the same or a higher concentration inside the support than outside the support. For example, when an alumoxane such as methylalumoxane is supported on silica, the preferred ratios of the aluminum to silica ratio outside the support particles over the aluminum to silica ratio inside the support particle is preferably about 2.0:1 or less even more preferably about 1:1 or less even more preferably about 0.85:1 or less.

In preferred catalyst compositions having greater than 50% by weight first fraction "primary" particles, prior to polymerization, substantially all of the AlO primary particles are substantially evenly dispersed over the total surface area of the support granules. By "substantially all" is meant at least 75%, preferably greater than 90% of the AlO particles or the transition metal compound-AlO complexes are dispersed in the support. By "substantially evenly" we mean that for any 25 square micron surface or greater of the support, the amount of alumoxane present is within 10% of the amount of alumoxane present in any other surface area of the same size. Likewise in another preferred embodiment the diameter of substantially all of the particles which are catalytically active is less than the mesopore diameter of the support.

The surface of the support over which the AlO or cyclopentadienyl transition metal compound-AlO (CpTM—AlO) particles are dispersed necessarily includes the internal surface of the support, i.e. the open-cell mesopores, but also includes dispersion over the external surface (including the interior macropores), which is considerably smaller. The dispersion will be present on those surfaces of the catalyst which are accessible to alumoxane loading and dispersion techniques. The most preferred catalyst system will contain highly dispersed AlO primary particles or AlO—CpTM particles, all or substantially all of which are located inside the mesopores of the support rather than on the exterior surface thereof. Thus at least 75% preferably, at least 90%, of the CpTm—AlO complex will exist inside the mesopores of the support. Further, the CpTM—AlO particles within the mesopores are substantially evenly dispersed over the total surface area of the support. The location of particles can be inferred from X-ray Photoelectron Spectroscopy (XPS), Low Voltage Scanning Electron Microscopy (LVSEM), High Resolution Analytical Electron Microscopy (AEM) measurements, as well as directly measured by Secondary Ion Mass Spectroscopy (SIMS), all of which are well known to those skilled in the respective arts.

XPS measurements made to determine any preferential disposition of AlO on the external surface of the support of the present invention showed no substantial Al accumulation on the external support surfaces of the freshly prepared catalyst. However, appreciable levels of Al were detected near or at the external surfaces of catalysts prepared from AlO's in which the large particle fraction was not separated prior to catalyst loading. One way to quantify the above preferred catalysts is to measure the ratios of aluminum from the alumoxane to an element in the support, (hereafter "support element") such as silica.

The aluminum to support element ratio is determined by X-ray Photoelectron Spectroscopy (XPS) normalizing to hydrogen and metals. For example, for a silica support, the aluminum to silicon ratio would be measured by XPS for the silica supported alumoxane and a crushed sample of the silica supported alumoxane. The ratio of the noncrushed (Al:Si) to crushed (Al:Si) directly correlates to the ratio of aluminum to silicon outside the support particles over the aluminum to silicon ratio inside the support particles mentioned in the preceding paragraph. (The word "crushed" refers to a finely ground solid, such as one that has been ground by mortar and pestal to a fine powder.) For example, if the XPS data show that the concentration of silicon is 16.37% and the concentration of aluminum is 8.04% in the first sample that is not crushed then the ratio of aluminum to silicon in that sample is 8.04 divided by 16.37 which is 0.491. When the sample is crushed, if the XPS shows that there is now 15.68% silicon and 10.29% aluminum, the aluminum to silicon ratio in the crushed sample is 10.29 divided by 15.68 which is 0.656. The ratio of aluminum outside to aluminum inside is then determined by dividing 0.491 by 0.656 to come up with a final ratio of 0.749. For the purposes of this invention it is assumed that the aluminum measured in the crushed samples that is from the "external" surface of the support particle is negligible when included in the total Aluminum.

Similar XPS data can be generated by methods known in the art for support materials other than silica and should be analyzed in the same manner as the silica example above. The preferred provision that the small AlO particles be well dispersed over the surface of the catalyst implies that there is not preferential desposition of the AlO or CpTM—AlO particles on the external surface. In other words, it signifies that the catalyst particles are substantially uniformly distributed throughout the internal and external surfaces of the catalysts. This uniform distribution is approached to the extent that the XPS measurements of the preferred catalyst indicate substantially no preferential disposition of the metallocene/MAO on the external surface of the support. Thus, this invention also provides for compositions comprising alumoxanes and supports and or alumoxane-transition metal complexes and supports having more alumoxanes on the inside than the outside. In particular the ratio of aluminum to support element outside to aluminum to support element inside should be about 2.0:1 or less, preferably about 1.5:1 or less, even more preferably about 1.0:1.0, even more preferred 0.85:1.0 or less. In the event that non-silicon supports are used, then the element selected for XPS study and comparison as discussed above would be the metal of the group 2,3,4 or 5 metal oxide, the silica of the silicates or the carbon of the polyolefin. In the event different supports are combined, the selected elemental ratios should also be combined. In the special case of alumina supports, one could measure the relative amounts of aluminium to carbon, since alumina supports do not contain carbon and the alumoxanes do. In that case the relevant ratio would be the ratio of the carbon to aluminum outside the support to the ratio of the carbon to aluminum inside the support.

A dominating feature of the alumoxane morphology is bimodal particle size distribution of the two dispersed colloidal fractions: (1) smaller 10 to 50 angstrom primary particles which remain in independent colloidal suspension; and (2) larger 200 to 10,000 angstrom secondary particles which agglomerate into networks of varying fractal dimension. Both types of AlO particles function as catalytic activators, however the smaller particles are preferred for use, especially in supported catalysts.

Generally one can observe secondary particles greater than or equal to 200 angstroms which aggregate, to some degree or another, into networks whose fractal dimensions vary somewhere between the diffusion limited and reaction limited extreme. These terms are discussed in detail in P. Meakin, "Simulations of Aggregation Processes" in *The Fractal Approach to Heterogeneous Chemistry: Surfaces, Colloids, Polymers*, edited by D. Avnin, John Wiley & Sons, Chichester, U.K. pp. 140–144, which is herein incorporated by reference.

Upon closer observation it is discovered that a large fraction of the alumoxane is comprised of non-aggregating particles which are an order of magnitude smaller i.e. less than or equal to about 50 angstroms than the network forming particles of about 200 angstroms or more. High resolution microscopy revealed the small primary particles to be comprised of even more finely divided particles of less than 10 angstroms.

The observation of alumoxane's, particularly methylalumoxane's, micro-morphology is consistent with some of its known properties, such as the propensity of its suspensions to stratify. The average pore size of typical carriers, nominally 200 angstroms for commercial silica, lies between the size ranges for the two alumoxane species. Thus, the smaller alumoxane fraction can easily penetrate into the carrier mesopores, but the larger particles cannot and ultimately are deposited as a coating on the support granule exterior. This can explain both reactor fouling and low bulk density.

We have noticed that AlO which is not diluted with very dry solvents turns cloudy almost immediately. This suggests that excess moisture also results in the formation in the larger particles and therefore the use of dry solvents is preferred to ensure that primary particles remain in suspension.

Additionally, the catalyst herein is characterized in that at least 75% of the transition metal compound activated AlO, prior to polymerization thereof, is dispersed in the form of particles having a diameter less than about 50 Å. Thus, if, for example, more than 25% of the AlO particles are dispersed in the form of particles measured to have diameters larger than about 200 Å, the catalyst exhibits reduced efficiency and activity maintenance. As measured by conventional bright field imaging in a transmission electron microscope with 5 Å point-to-point resolution, as well as by high resolution (less than 4 Å point-to-point) bright field imaging in a dedicated scanning transmission electron microscope, and by high resolution secondary imaging in a low voltage scanning electron microscope with less than 20 Å point-to-point resolution at 15 keV incident beam energy, the particle size in the most preferred catalyst of this invention is found to be such that no more than 2 wt. % of the AlO is dispersed in the form of particles measured to be about 200 Å or greater in diameter.

Alumoxane, particularly methylalumoxane, is a multiple colloid which exhibits a complex hierarchical microstructure within its dispersed phase. It has two clearly discrete levels: smaller ($\leq 50$ Å) primary particles, and larger ($\geq 200$ Å) secondary particles. These particles are clustered in primarily two configurations, including the deposition of the less than 50 Å particles as non interactive, freely flowing granules which have limited natural affinity for each other and, consequently, are mobile and flow freely around each other in hydrocarbon solvent. Large populations from which the solvent has evaporated are highly nonconducting and appear as dried mudflats at lower magnifications, but have distinctive granular "flow" patterns at high magnifications. The larger than 200 Å particles exhibit relative degrees of affinity as manifested by their propensity to agglomerate into networks with various fractal dimensions.

The dominating microstructural feature is the bimodal particle size distribution of two dispersed colloidal fractions:"smaller" 10–190 angstrom primary particles which remain independent in colloidal suspension, and "larger", 200–10,000 Angstrom secondary particles which agglomerate into networks of varying fractal dimension. Both types of alumoxane particles function with cyclopentadienyl transition metal compounds as a catalyst system, however, the secondary particles contain relatively large volumes of interior Al atoms which serve no catalytic function but do increase the overall Al to transition metal ratio [Al/M]. Varying the relative populations of primary and secondary particles provides control over [Al/M] in any given catalyst system increases efficiency and reduces cost. A CpTM—AlO catalyst system comprising the primary particles described above requires less total alumoxane than a catalyst system predominately comprising large alumoxane particles because in the first instance "all" of the AlO is accessible to both monomer and CpTm compounds whereas in the second instance a fair amount of the AlO is inaccessible and "locked" inside the support and the larger secondary particles.

The size of the alumoxane particles may be measured using high resolution electron microscopy. In this procedure the sample is prepared by placing a small droplet of highly diluted (100:1 in toluene) MAO from a very well-shaken bottle on a Si single crystal wafer (an atomically smooth, conducting support surface for LVSEM), or a perforated carbon coated Cu grid (for TEM and STEM). After complete drying in a glove box the sample is enclosed in a transfer vessel and then loaded into the microscope inside an $N_2$ purge bag (or STEM high vacuum ante-chamber).

As is now well known, alumoxanes can be prepared by various procedures. For example, a trialkyl aluminum may be reacted with water, in the form of a moist inert organic solvent; or the trialkyl aluminum may be contacted with a hydrated salt, such as hydrated copper sulfate suspended in an inert organic solvent, to yield an alumoxane. Generally, however prepared, the reaction of a trialkyl aluminum with a limited amount of water yields a mixture of both linear and cyclic species of alumoxane.

Suitable alumoxanes which may be utilized in this invention are those prepared by the hydrolysis of a trialkylaluminum, such as trimethylaluminum, triethylaluminum, tripropylaluminum, triisobutylaluminum, dimethylaluminum chloride, diisobutylaluminum chloride, diethylaluminum chloride and the like. The most preferred alumoxane for use is methylalumoxane (MAO). Methylalumoxanes having an average degree of oligomerization of from about 4 to about 25 ("p"=4 to 25), with a range of 13 to 25 are the most preferred.

A typical alumoxane will contain free trisubstituted or trialkyl aluminum, bound trisubstituted or trialkyl aluminum, and alumoxane molecules of varying degree of oligomerization. Those methylalumoxanes most preferred contain lower levels of trimethylaluminum. Lower levels of trimethylaluminum can be achieved by reaction of the trimethylaluminum with a Lewis base or by vacuum distillation of the trimethyl aluminum or any other means known in the art.

The cylcopentadienyl transition metal compounds that can be utilized with alumoxanes as active olefin catalysts include that class of catalysts described and disclosed in U.S. Pat. Nos. 5,055,438, 5,057,475, 5,096,867, 5,017,714; 4,808,561 copending U.S. Ser. No. 07/468,382 filed on Feb. 28, 1990, now abandoned. European Patent Application 520732, published Dec. 30, 1992 and EPA 129 368 published Dec. 27, 1984 all of which are herein incorporated by reference.

In general these catalyst systems comprise two parts. A first part being a cyclopentadienyl transition metal compound and second part being an alumoxane. Typically a cyclopentadienyl transition metal compound such as biscyclopentadienyl zirconium dichloride, cyclopentadienyl titanium dimethyl, biscyclopentadienyl hafnium dimethyl, and the like are combined either before or after the addition of monomer or support with an alumoxane preferably methylalumoxane.

The CpTm—AlO catalysts of this invention can also be supported by methods disclosed in U.S. Pat. Nos. 4,808,561; 4,897,455; 5,057,475; and U.S. patent application Ser. No. 459,921 filed on Nov. 02, 1990, now abandoned (published as PCT International publication WO 91/09882) which are herein incorporated by reference.

The catalysts of this invention can be used to polymerize linear, branched, and/or cyclic olefins particularly ethylene and $C_3$ to $C_{100}$, preferably ethylene and $C_3$ to $C_{30}$ alpha olefins even more particularly one or more of ethylene, propylene, butene, pentene, 3-methyl-pentene-1, cyclohexene, norbornene, hexene, octene, isobutene, 3,5,5-trimethylhexene-1 and the like. In a preferred embodiment, terpolymers of ethylene, propylene and a non-conjugated diene are produced.

The choice of catalyst involved will depend on the final polymer desired and will be apparent to those ordinary skill in the art upon reading the disclosures of the cases incorporated above. For example, it is disclosed in the above cases that monocyclopentadienyl titanium complexes tend to incorporate monomers at a higher rate than biscyclopentadienyl zirconium complexes. Thus, if higher percentage of co-monomer were desired in a co-polymer then a monocyclopentadienyl catalyst could be chosen. Likewise, it has been disclosed in the cases above that substitutions on the various cyclopentadienyl rings can affect polymer tacticity and molecular weight.

The polymerization reactions can take place in solution, gas phase, slurry or bulk phase as deemed appropriate by those of ordinary skill in the art. If the reactions take place in solution phase, hydrocarbon diluents are preferred. Inert hydrocarbons such as hexane, pentane, aromatics, toluene, xylene and the like are just a few of the useful hydrocarbons that one of ordinary skill in the art can utilize. Preferred supported catalysts and alumoxanes of this invention are used in gas phase or slurry.

This invention also provides for alumoxane compositions having 50% by weight or more of particles having a average diameter of 50 Angstroms or less, preferably 70% by weight, even more preferably 80% by weight. In a typical polymerization an alumoxane would be decanted from the clear phase of a commercial aluminumoxane solution that had been allowed to settle over a period of time. That alumoxane could then be filtered to remove large particles and then placed on a support preferably silica which had been dehydrated and dried beyond the solvent vapor point. Preferably, the alumoxane is placed in solution with the cyclopentadienyl transition metal catalyst, placed on the support, metered into a gas phase reactor with monomer, allowed to react at a sufficient temperature and pressure and then recovering the polymer product formed.

The polymer products formed are unique in that not only do they have a molecular weight distribution of four or less, preferably three or less, even more preferably 2.5 or less, but they also have a very desirable uniform average particle size.

These polymers have very desirable bulk densities. High bulk density is generally correlated with the ability to pack more polymer in a smaller space and is a very desirable characteristic from a commercial aspect. Bulk density of a sample is measured by dividing the weight of the sample by volume of the sample. (Bulk density is reported in units of g/cc or lb/ft$^3$ (0.0160 g/cc=1 lb/ft$^3$.) The polymer products of this invention have a bulk density of 25 lb/ft$^3$ (0.4 g/cc).

Likewise, the process of this invention also provides polymers with a lower or wider dispersion of residual metal ash in the polymer. Ash is generally measured by ICPES (Inductively Coupled Plasma Emission Spectroscopy, which is described in "J. W. Olesik, "Inductively Coupled Plasma-Optical Emission Spectroscopy," in Encyclopedia of Materials Characterization, C. R. Brundle, C. A. Evans, Jr. ans S. Wilson, eds., Butterworth-Heinemann, Boston, Mass. (1992) pp.633–644). The polymers of this invention preferably have an ash content of less than 100 ppm. Thus, this invention also provides a method for enhancing bulk density or controlling bulk density and for enhancing or controlling ash content.

EXAMPLES

Molecular weight determinations for polyolefin products were made by Gel Permeation Chromatography (GPC) according to the following technique. Molecular weights and molecular weight distributions were measured using a Waters 150 gel permeation chromatograph equipped with a differential refractive index (DRI) detector and a Chromatix KMX-6 on-line light scattering photometer. The system was used at 135° C. with 1,2,4-trichlorobenzene as the mobile phase. Shodex (Showa Denko America, Inc.) polystyrene gel columns 802, 803, 804 and 805 were used. Mw/Mn was calculated from elution times. The numerical analyses were performed using the commercially available Beckman/CIS customized LALLS software in conjunction with the standard Gel Permeation Chromotography software package.

Calculations involved in the characterization of polymers by $^{13}$ CNMR follow the work of F. A. Bovey in "Polymer Conformation and Configuration" Academic Press, New York, 1969.

All experiments were carried out in nitrogen purged dry boxes. All solvents were purchased from commercial sources and were nitrogen purged or distilled and dried over activated molecular sieves. Aluminum Alkyls were purchased as 20–25 wt % solutions from commercial sources. The methylalumoxane (MAO) was purchased as 30 wt % in toluene from Schering.

Clear decanted MAO/catalyst preparation.

A filtered Solution of (dimethyl-siladiyl) bis(tetrahydroindenyl)-zirconium dichloride in toluene (50 ml) was added with stirring to the clear, decanted MAO supernatant solution (Schering 30 weight % MAO, 90.4 ml). After ten minutes the solution was amber and clear. To this was added dehydrated silica (20.0 g, Davidson 948 regular, 800° C. dehydration) and stirred fifteen minutes. This slurry was evaporated on a rotoevaporated at 65° C. over twenty minutes at which point the slurry had reached a "mud" stage. After drying a total of about two hours at 60–65° C. the solids were recovered as a light orange solid (36.75 g).

In a clean, dry two liter autoclave which had been flushed with propylene vapor, TEAL (triethylaluminum)(0.8 ml, 1.5 M in heptane) was added. The reactor was closed and filled the 750 milliliters of liquid propylene. With the reactor temperature at 30° C., the catalyst (as an 18 wt % oil slurry) was washed in via an addition tube with 250 mls of propylene. The reactor was rapidly heated to 65° C. After 30 minutes the reactor was cooled and the excess propylene vented. The polymer was removed and dried. The polymer came out of the reactor free of chunks and fouling.

The polymer analysis was carried out as described in U.S. Pat. No. 5,026,798 and U.S. Pat. No. 5, 017,714 herein incorporated by reference. DSC melting points were determined on a commercial DSC instrument and are reported as the second melting point. The catalysts and data are reported in Table 2.

TABLE 2

| Exp | Catalyst Amount (mgs) | Catalyst Activity (Kg/g/hr) | DSC Mp (° C.) | Mw (×10³) | Mw/Mn (MWD) |
|---|---|---|---|---|---|
| 1 | 104 | 0.96 | 137.2 | 43.9 | 2.4 |

Example 2

Several examples were run according to the procedure listed above. The data and conditions are described in Table 3.

Catalyst 1 ((1,3 methyl,butyl-Cp)$_2$ZrCl$_2$ ) activated with MAO in toluene added to dry silica.

Catalyst 2 (dimethylysilyl bis-tetrahydroindenyl zirconium dichloride (Me$_2$Si(H$_4$Ind)$_2$ZrCl$_2$)) activated with methylalumoxane was prepared by the method disclosed in U.S. Ser. No. 885,170, issued as U.S. Pat. No. 5,240,894,i.e. the transition metal component was added to the MAO in toluene, dry silica was added to the combination and the solvent was dried off.

Catalyst 3 was the same as catalyst two, except only the supernatant liquid decanted off the top of an aged bottle of MAO was used.

TABLE 3

| Catalyst | XPS-Pristine | XPS-Crushed | BET SA (M²/g) |
|---|---|---|---|
| 1 | AL/Si = 2.79 | Al/Si = 0.78 | 221 |
| 2 | Al/Si = 200 | AL/Si = 0.97 | 228 |
| 3 | Al/Si = 0.48 | Al/Si = 0.66 | 84 |
| Pure MAO on Silica | Al/Si = 1.56 | Al/Si = 0.55 | — |
| Pure Silica | — | — | 360 |

BET = Brunauer-Emmet-Teller method (a gas adsorption and desorption technique routinely used to furnish information about pore structure.)

As is apparent from the foregoing description the materials prepared and the procedures followed relate to specific embodiments of the broad invention. It is apparent from the foregoing general description and the specific preferred embodiments that while forms of the invention have been illustrated and described, various modifications can be made without departing from the spirit and scope of this invention. Accordingly it is not intended that the invention be limited thereby.

We claim:

1. A composition comprising alumoxane and porous support wherein the ratio of (1) to (2) is 2.0 or less wherein (1) is the ratio of aluminum to the support element on the external surface area of the support and (2) is the ratio of aluminum to the support element on the internal surface area of the support.

2. The composition of claim 1 further comprising a cyclopentadienyl transition metal compound.

3. The composition of claim 2 wherein the support has been dehydrated prior to contacting with the cyclopentadienyl compound and the alumoxane.

4. The composition of claim 1 or 2 wherein the ratio of (1) to (2) is 1.5 or less.

5. The composition of claim 1 or 2 wherein the ratio of (1) to (2) is 0.85 or less.

6. The composition of claim 1 or 2, wherein the support is silica and wherein greater than 90% of the alumoxane used to prepare the composition is composed of particles having an average diameter of less than 50 Å.

7. The composition of claim 6 wherein the support is silica and the alumoxane is methylalumoxane.

8. The composition of claim 1 or 2, wherein the support has been dehydrated by heating to 800° C. or more prior to contact with the cyclopentadienyl compound and the alumoxane.

9. A composition comprising alumoxane having an average particle size of less than 50 Å, a cyclopentadienyl transition metal compound and silicon wherein the ratio of (1) to (2) is 1.5 or less wherein (1) is the ratio of aluminum to silicon on the external surface area of the support and (2) is the ratio of aluminum to silicon on the internal surface area of the support.

10. The composition of claim 9 wherein the ratio of (1) to (2) is 0.85 or less.

11. The composition of claim 9, wherein the alumoxane is methylalumoxane.

12. An alumoxane containing catalyst system wherein said alumoxane consists essentially of alumoxane particles of 20 nanometers diameter or less.

13. A catalyst system consisting essentially of alumoxane particles of up to about 5 nanometers in diameter and a cyclopentadienyl transition metal compound.

14. The catalyst composition of claim 13 further comprising a support.

15. The catalyst system of claim 13 wherein the cyclopentadienyl transition metal compound is a bis-cyclopentadienyl group 4 transition metal compound.

* * * * *

(12) REEXAMINATION CERTIFICATE (4645th)
United States Patent
Butler et al.

(10) Number: US 5,902,766 C1
(45) Certificate Issued: Sep. 17, 2002

(54) ALUMOXANES, CATALYSTS UTILIZING ALUMOXANES AND POLYMERS THEREFROM

(75) Inventors: Jeffrey Harold Butler, Baytown, TX (US); Terry John Burkhardt, Kingwood, TX (US)

(73) Assignee: Exxon Chemical Patents Inc., Wilmington, DE (US)

Reexamination Request:
No. 90/005,833, Nov. 1, 2000

Reexamination Certificate for:
Patent No.: 5,902,766
Issued: May 11, 1999
Appl. No.: 08/532,039
Filed: Sep. 21, 1995

Related U.S. Application Data

(63) Continuation of application No. 08/180,171, filed on Jan. 11, 1994, now abandoned.

(51) Int. Cl.$^7$ ............................... C08F 4/52; C08F 4/42
(52) U.S. Cl. ................... 502/152; 502/120; 526/160; 526/943; 556/179
(58) Field of Search ................................. 502/152, 120; 556/179; 526/160, 943

(56) References Cited

U.S. PATENT DOCUMENTS

| | | |
|---|---|---|
| 4,808,561 A | 2/1989 | Welborn, Jr. |
| 4,921,825 A | 5/1990 | Kioka et al. |
| 5,001,205 A | 3/1991 | Hoel |
| 5,055,438 A | 10/1991 | Canich |
| 5,057,475 A | 10/1991 | Canich et al. |
| 5,093,295 A | 3/1992 | Tomotsu et al. |
| 5,124,418 A | 6/1992 | Welborn, Jr. |
| 5,157,137 A | 10/1992 | Sangokoya |
| 5,191,052 A | 3/1993 | Welborn, Jr. |
| 5,240,894 A | 8/1993 | Burkhardt et al. |
| 5,276,208 A | 1/1994 | Winter et al. |

FOREIGN PATENT DOCUMENTS

| | | |
|---|---|---|
| EP | 0206794 | 12/1986 |
| EP | 0232595 | 8/1987 |
| EP | 0295312 | 12/1987 |
| EP | 0260130 | 3/1988 |
| EP | 0336593 | 10/1989 |
| EP | 0393358 | 3/1990 |
| EP | 0442300 | 8/1991 |
| WO | 9319073 | 9/1993 |

OTHER PUBLICATIONS

Cam et al., "Characterization of Methylalumoxane by Means of Gel Permeation Chromatography", Makromol. Chem 191:1641–1647 (1990).

Galli et al., "High Yield Catalysts in Olefin Polymerization", Die Angewandte Makromolekulare Chem. 120:73–90 (1984).

Hutchinson et al., "Polymerization of Olefins through Heterogeneous Catalysis X: Modeling of Particle Growth and Morphology", Journal of Applied Polymer Sciences, 44:1389–1414 (1992).

Niegisch et al., "Characterization Techniques for the Study of Silica Fragmentation in the Early Stages of Ethylene Polmerization", Macromolecules, 25:3910–3916 (1992).

Opposition Paper of BP Chemicals Ltd.
Opposition Paper of Borealis Technology Oy.
Opposition Paper of Elenac GmbH.
Opposition Paper of Targon GmbH including Test Report.

*Primary Examiner*—Fred Teskin

(57) ABSTRACT

A catalyst which exhibits superior control of product particle size in the insertion polymerization of alpha-olefins is described as transition metal compounds which associate with non-coordinating alumoxane anions which are dispersed throughout the interior of a silica support in the form of particles which are less than or equal to about 50 Å (5 nanometers) in diameter. This catalyst is capable of gas phase (e.g. heterogeneous) polymerization of propylene into product granules with a high degree of control over granule particle size distribution and bulk density.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–15 is confirmed.

\* \* \* \* \*